(12) United States Patent
Garcia (10) Patent No.: US 7,769,548 B2
(45) Date of Patent: Aug. 3, 2010

(54) MICROARRAY ANALYTICAL DATA STITCHING SYSTEM AND METHOD

(75) Inventor: Francisco Jose Garcia, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 688 days.

(21) Appl. No.: 11/801,535

(22) Filed: May 10, 2007

(65) Prior Publication Data

US 2008/0281527 A1    Nov. 13, 2008

(51) Int. Cl.
*G06F 19/00* (2006.01)
*G06K 9/40* (2006.01)

(52) U.S. Cl. ................... 702/19; 382/128; 382/268
(58) Field of Classification Search .............. None
See application file for complete search history.

(56) References Cited

U.S. PATENT DOCUMENTS

| 6,355,431 | B1 | 3/2002 | Chee et al. |
| 6,544,732 | B1 | 4/2003 | Chee et al. |
| 6,620,584 | B1 | 9/2003 | Chee et al. |
| 6,812,005 | B2 | 11/2004 | Fan et al. |
| 6,839,454 | B1 | 1/2005 | Park |
| 6,890,741 | B2 | 5/2005 | Fan et al. |
| 6,890,764 | B2 | 5/2005 | Chee et al. |
| 6,913,884 | B2 | 7/2005 | Stuelpnagel et al. |
| 7,033,754 | B2 | 4/2006 | Chee et al. |
| 7,116,809 | B2 | 10/2006 | Bartell |
| 7,166,431 | B2 | 1/2007 | Chee et al. |
| 2003/0133009 | A1* | 7/2003 | Brown et al. ........... 348/61 |
| 2006/0083428 | A1 | 4/2006 | Ghosh et al. |

FOREIGN PATENT DOCUMENTS

| WO | WO9908233 A1 | 2/1999 |
| WO | WO2005055145 A1 | 6/2005 |

* cited by examiner

*Primary Examiner*—John S Brusca
(74) *Attorney, Agent, or Firm*—Fletcher Yoder PC (57) ABSTRACT

A technique is provided for analyzing image data for biological microarrays. Images are made of multiple swaths in multiple passes of an imaging system. Sites encoded by the image data are assigned a value and these values are indexed by site location. An overlapping region of the swaths may be identified by analysis of the indexed site values. The site values for all image sites are then stitched and the data is integrated and stored for later analysis.

24 Claims, 5 Drawing Sheets

MICROARRAY ANALYTICAL DATA STITCHING SYSTEM AND METHOD

BACKGROUND

The present invention relates generally to the field of data processing systems for analyzing biological microarrays. More particularly, the invention relates to techniques for integrating data derived from multiple images made of such microarrays.

An increasing number of applications have been developed for biological microarrays. Such microarrays typically include deoxyribonucleic acid (DNA) and ribonucleic acid (RNA) probes. These are specific for nucleotide sequences present in genes in humans and other organisms. In certain applications, for example, individual DNA and RNA probes can be attached at small locations in a geometric grid (or randomly) on a microarray support. A test sample, such as from a known person or organism, can be exposed to the grid, such that complimentary genes of fragments hybridize to probes at the individual sites in the array. The array can then be examined by scanning specific frequencies of light over the sites to identify which genes or fragments in the sample are present, by fluorescence of the sites at which genes or fragments hybridized.

In similar applications, biological microarrays may be used for genetic sequencing and similar applications. In general, genetic sequencing consists of determining the order of nucleotides or nucleic acid in a length of genetic material, such as a fragment of DNA or RNA. Relatively short sequences are typically analyzed, and the resulting sequence information may be used in various bioinformatics methods to logically fit fragments together so as to reliably determine the sequence of much more extensive lengths of genetic material from which the fragments were derived. Automated, computer-based examination of characteristic fragments have been developed, and have been used more recently in genome mapping, identification of genes and their function, and so forth.

For these and other applications of biological microarrays, improvements have recently been made in imaging systems for capturing data related to the individual molecules attached at sites of the microarrays. For example, improvements in imaging systems allow for faster, more accurate and higher resolution scanning and imaging, particularly through the use of line-scanning and confocal control of imaging optics. However, as the density of microarrays increases, and the size of the areas containing individually characterized sites also increases, scanning, both by point scanning and line scanning approaches becomes problematic. In particular, depending upon the limitations of the scanner, a pre-defined area of a microarray area or site grid may be too large to be scanned in a single pass by the scanning system. Consequently, information gathered from a scanning pass will be incomplete unless associated with that of other scanning passes for the overall area.

Conventional techniques may be used to piece together images of the scanned regions of microarrays. However, such techniques require extensive memory and computational capacities. Simply stitching images together does not result in a time or computationally efficient approach to analysis of the image data acquired of the microarrays.

There is a need, therefore, for an improved technique for analyzing image data in multiple imaging passes over a biological microarray. There is a particular need for techniques that will allow rapid and accurate integration of data from multiple imaging passes, permitting improved throughput for diagnostic, encoding, sequencing, and other operations performed with the microarrays.

BRIEF DESCRIPTION

The present invention provides a novel approach to microarray image analysis designed to respond to such needs. The technique may be employed with any type of microarray, including those having individual sites disposed in various grid patterns, rectangular, hexagonal, random, and so forth. Moreover, the technique may be used in any suitable application, including diagnostic applications, sequencing applications, gene expression experiments and analysis, and so forth. Still further, the technique may be used for analysis of microarrays to which a variety of biological materials have been attached or propagated, such as DNA, RNA, other oligonucleotides, and indeed other classes of molecules. Finally, the technique may be used with various imaging systems, including point scanning approaches, line scanning imagers, and imagers that use one or more of various wavelengths for acquiring reflected or fluoresced light for imaging purposes.

In accordance with one aspect of the invention, a method is provided for analyzing biological microarray image data. The method includes accessing image data for a plurality of imaged swaths of the microarray, and assigning a value to each of a plurality of sites in each swath based upon the image data. Each site value is then associated with a corresponding location index. The site values for the swaths are then combined based upon the location indices. The resulting dataset includes the locations and detected characteristics for sites from multiple swaths. An advantage of the method is that deriving information of interest from multiple image swaths of an array and combining the information provides a more efficient way to stitch together a data set covering the entire array than the alternative of aligning images to arrive at a composite image of the array. This increased efficiency is due, at least in part, to the reduced computer memory required to manipulate the datasets created in the methods compared to the memory typically required to manipulate the images from which they are derived.

The values assigned to the sites may be based upon analysis of pixel values for clusters or groups of pixels corresponding to each site. Moreover, the values may be combined by selecting only one of a pair (or more) of the values for the same sites that may be imaged in an overlapping region of the swaths.

The location indices may be associated with the site values in various ways. For example, edges of imaged regions, fiducial marks in an overlapping region, unique spatial patterns of sites in an overlapping region or other characteristic features near or in the swaths may be used to determine which values correspond to which sites having known locations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
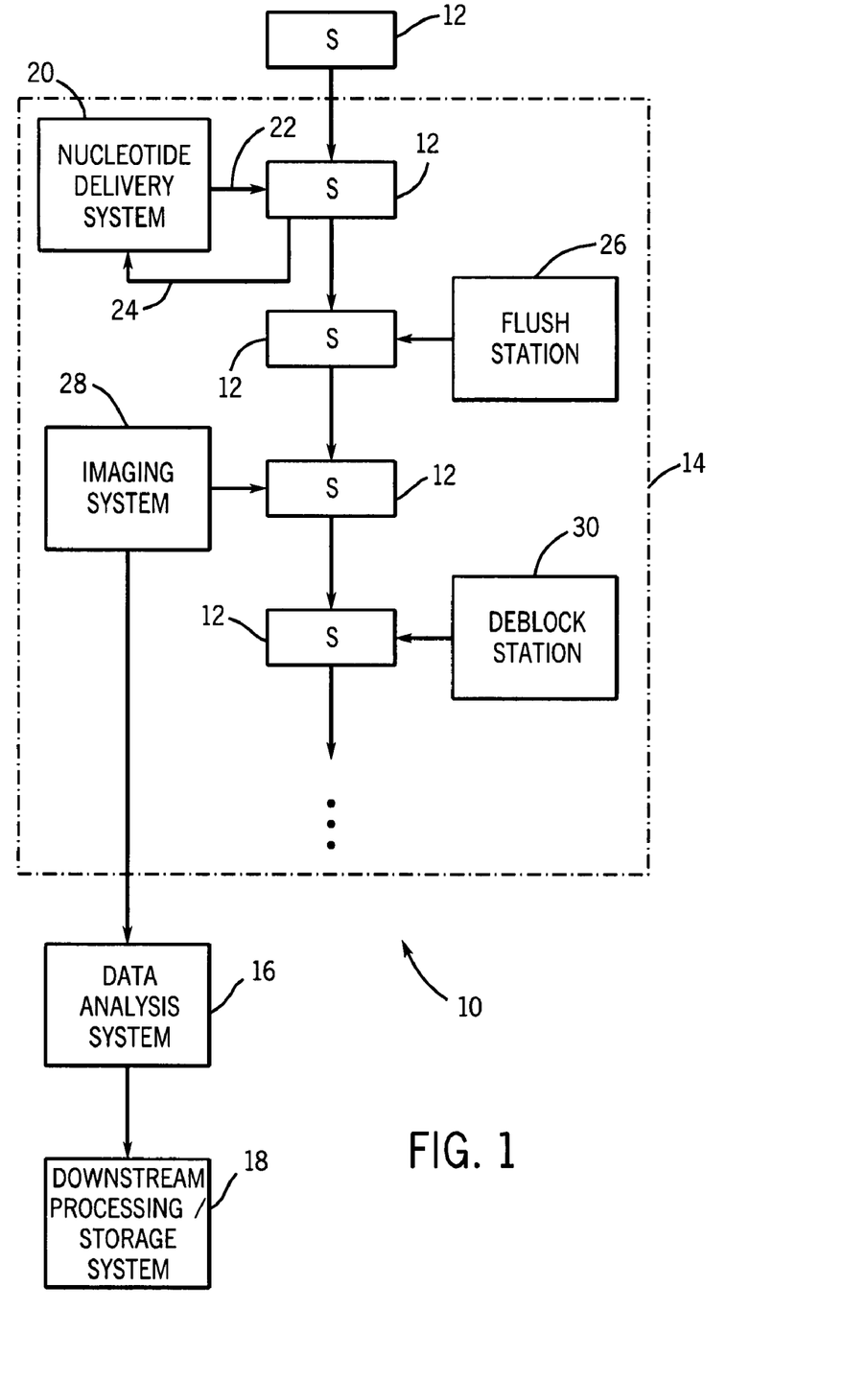
FIG. 1 is a diagrammatical overview of a biological microarray imaging and image processing system employing aspects of the present invention.

Turning now to the drawings, and referring first to FIG. 1, an exemplary analysis system 10 is illustrated for processing biological microarrays, imaging the microarrays, and analysis of data based upon the images. In the illustrated embodiment, the system is designed to introduce molecules, such as nucleotides, oligonucleotides, and other bioactive reagents into samples 12 that may be prepared in advance. The system may be designed for synthesizing biopolymers, such as DNA chains, or sequencing biopolymers. However, it should be borne in mind that the present technique is not limited in any way to sequencing operations, gene expression operations, diagnostic applications, diagnostic applications, or any one of these, but may be used in any of them for analyzing collected image data for multiple swaths or passes over a region of a sample as described below. Other substrates containing arrays of molecules or other detectable features can similarly be used in the techniques and systems set forth herein.

In the illustrated embodiment, however, exemplary biopolymers might include, but are not limited to, nucleic acids, such as DNA, RNA or analogs of DNA or RNA. Other exemplary biopolymers might include proteins (also referred to as polypeptides), polysaccharides or analogs thereof. Although any of a variety of biopolymers may be used, for the sake of clarity, the systems and methods used for processing and imaging in the exemplary context illustrated in FIG. 1 will be described with regard to processing of nucleic acids. In general, the system illustrated in FIG. 1 will act upon samples 12 which may include one reaction site or an array of reaction sites. As used herein, the term "array" or "microarray" refers to a population of different reaction sites on one or more substrates such that different reaction sites can be differentiated from each other according to their relative location. Typically, a single species of biopolymer may be attached to each individual reaction site. However, multiple copies of particular species of biopolymer can be attached to a particular reaction site. The array taken as a whole will typically include a plurality of different biopolymers attached at a plurality of different sites. Reaction sites can be located at different addressable locations on the same substrate. Alternatively, an array can include separate substrates, such as beads, each bearing a different reaction site. The sites may include fragments of DNA attached at specific locations in an array or may be wells in which a target product is to be synthesized. In certain applications, the system may be designed for continuously synthesizing or sequencing molecules, such as polymeric molecules based upon common nucleotides.

In the diagrammatical representation of FIG. 1, analysis system 10 may include a processing system 14 designed to process samples, typically biological microarrays, and generate image data representative of individual sites on the microarray, as well as spaces between sites. A data analysis system 16 receives the image data and processes the image data in accordance with the present invention, to extract meaningful values from the imaging data as described below. A downstream processing/storage system 18, then, may receive this information and store the information, along with imaging data, where desired. The downstream processing/storage system may further analyze the image data or the data derived from the image data, such as to diagnose medical conditions, compile sequencing lists, analyze gene expression, and so forth.

The processing system 14 may employ a bio-molecule reagent delivery system 20 for delivering various reagents to a sample 12 as it progresses through the system. In general, system 14 may include a plurality of stations through which samples and sample containers progress. This progression can be achieved in a number of ways including, for example, physical movement of the sample to different stations, physical movement of different stations to a sample, delivery of fluid from different stations to a sample such as via valve actuation or some combination thereof. A system may be designed for cyclic operation in which reactions are promoted with single nucleotides or with oligonucleotides, followed by flushing, imagining and de-blocking in preparation for a subsequent cycle. In a practical system, the samples may be circulated through a closed loop path for sequencing, synthesis, ligation, or any other suitable process. Again, it should be noted that the process illustrated in FIG. 1 is by no means limiting, and the present invention may operate on image data acquired from any suitable system employed for any application.

In the illustrated embodiment, the nucleotide delivery system 20 provides a process stream 22 to the samples 12. An effluent stream 24 from the container may be recaptured and recirculated in the nucleotide delivery system. In the illustrated embodiment, then, the sample container may be flushed at a flush station 26 to remove additional reagents and to clarify the sample for imaging. The sample is then moved to an imaging system 28 where image data may be generated that can be analyzed for determination of the sequence of a progressively building nucleotide chain, such as based upon a template. In a presently contemplated embodiment, for example, imaging system 28 may employ confocal line scanning to produce progressive pixilated image data that can be analyzed to locate individual sites in an array and to determine the type of nucleotide that was most recently attached or bound to each site. Other imaging techniques may also suitably be employed, such as techniques in which one or more points of radiation are scanned along the sample.

Following imaging station 28, then, the samples may progress to de-blocking station 30 in which a blocking molecule or protecting group is cleaved from the last added nucleotide, along with a marking dye. If system 14 is used for sequencing, by way of example, image data from the imaging system 24 will be stored and forwarded to a data analysis system as indicated generally at reference numeral 16.

The analysis system will typically include a general purpose or application-specific programmed computer providing for user interface and automated or semi-automated analysis of the image data to determine which of the four common DNA nucleotides was last added at each of the sites in an array of each sample, as described below. As will be appreciated by those skilled in the art, such analysis is typically performed based upon the color of unique tagging dyes for each of the four common DNA nucleotides. This image data may be further analyzed by the downstream processing/storage system 18, which may store data derived from the image data as described below, as well as the image data itself, where appropriate. Again, the sequencing application is intended to be one example only, and other operations, such as diagnostic applications, clinical applications, gene expression experiments, and so forth may be carried out that will generate similar imaging data operated on by the present invention. Some examples of array based methods that generate image data that can be made and used in accordance with the teachings herein include, array-based genotyping or expression analyses as described, for example, in WO 2005/003304, US 2005/0181394, US 2005/0059048, US2005/0053980, US 2005/0037393, US2004/0259106, US 2004/0259100 or decoding to determine the position of particular probes in random arrays as described, for example, in Gunderson et al., *Genome Research*, 14: 870-877 (2004); U.S. Pat. No. 7,033,754 or US 2003/0157504. The above references are incorporated herein by reference.

Figure 2:
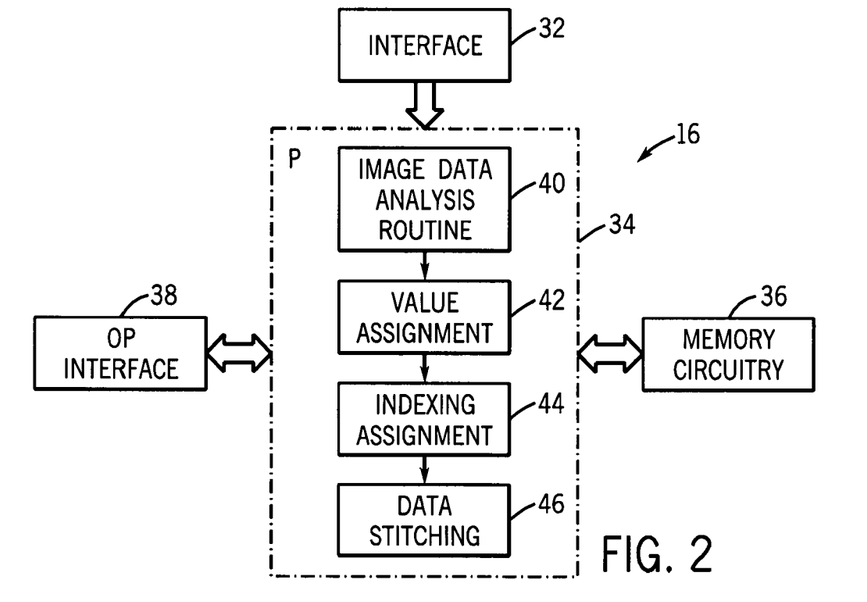
FIG. 2 is a diagrammatical overview of certain of the functional components that may be included in a data analysis system for use in a system of the type illustrated in FIG. 1.

FIG. 2 illustrates an exemplary data analysis system 16 and certain of its functional components insomuch as they relate to the present invention. As noted above, the system will typically be formed by one or more programmed computers, with programming being stored on one or more machine readable media with code executed to carry out processes described herein. In the illustrated embodiment, for example, the system includes an interface 32 designed to permit networking of the system to one or more imaging systems acquiring image data of biological microarrays. The interface may receive and condition data, where appropriate. In general, however, the imaging system will output digital image data representative of individual picture elements or pixels that, together, form an image of the biological microarray. A processor, denoted generally by reference numeral 34 in FIG. 2, processes the received image data in accordance with a plurality of routines defined by processing code. The processing code may be stored in various types of memory circuitry, as represented generally by reference numeral 36 in FIG. 2.

In accordance with the presently contemplated embodiments of invention, the processing code executed on the image data includes an image data analysis routine 40 designed to analyze the image data to determine the locations of individual sites visible or encoded in the image data, as well as locations in which no site is visible (i.e., where there is no site, or where no meaningful radiation was detected from an existing site). As will be appreciated by those skilled in the art, in a typical biological microarray imaging setting, locations in the microarray, either laid out in a grid pattern or randomly, will typically appear brighter than non-site locations due to the presence of fluorescing dyes attached to the imaged molecules. It will be understood that the sites need not appear brighter than their surrounding area for example when a target for the probe at the site is not present in a sample being detected. The color at which individual sites appear may be a function of the dye employed as well as of the wavelength of the light used by the imaging system for imaging purposes. Sites to which targets are not bound or that are otherwise devoid of a particular label can be identified according to other characteristics such as their expected location in the microarray.

Once the image data analysis routine 40 has located individual sites in the image data, a value assignment may be carried out as indicated at reference numeral 42. In general, the value assignment carried out at step 42 will assign a digital value to each site based upon characteristics of the image data represented by pixels at the corresponding location. That is, for example, the value assignment routine 42 may be designed to recognize that a specific color or wavelength of light was detected at a specific location, as indicated by a group or cluster of pixels at the location. In a typical DNA imaging application, for example, the four common nucleotides will be represented by separate and distinguishable colors. Each color, then, may be assigned a value corresponding to that nucleotide. The value assignment carried out by routine 42, then, will assign the corresponding value to the entire site, alleviating the need to further process the image data itself, which will typically be much more voluminous (i.e., many pixels may correspond to each site) and of significantly larger numerical values (i.e., much larger number of bits to encode each pixel).

An indexing assignment routine 44, then, will associate each of the assigned values with a location in an image index or map. As described more fully below, the map will correspond to the known or determined locations of individual sites within the sample. The present technique allows for indexing the assigned values by reference to one or more known features, such as an edge, a notch, a particular pattern, a fiducial marker, and so forth.

Finally, as described in greater detail below, a data stitching routine 46 may be carried out to integrate data from multiple scans of the microarray. Because the microarray, or a region of the microarray may be scanned in multiple passes, the data stitching carried out in routine 46 will allow for the resulting data to be integrated, joining indexed values from different scans of the microarray into a combined dataset.

It may be noted that as in the illustration of FIG. 2, an operator interface 38 is typically provided, which may consist of a conventional computer monitor, keyboard, mouse, and so forth to interact with the routines executed by the processor 34. The operator interface may be used to control, visualize or otherwise interact with the routines as imaging data is processed, analyzed and resulting values are indexed and stitched.

Figures 3, 4:
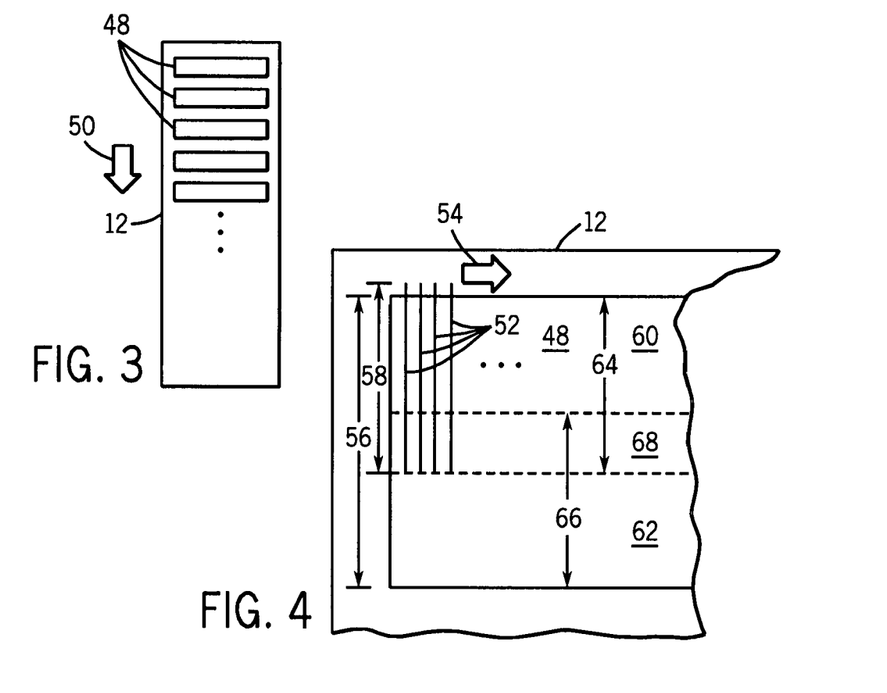
FIG. 3 is a plan view of an exemplary biological microarray of the type that may be used in conjunction with the present invention.
FIG. 4 is an enlarged portion of the microarray of FIG. 3 illustrating swaths scanned for acquisition of image data to be used in the present analysis technique.

FIG. 3 illustrates an exemplary sample or microarray 12. As shown in FIG. 3, a plurality of grids 48 may be provided that each will include a multitude of individual sites to be imaged. A wide range of layouts for such microarrays are possible, and the invention is not intended to be limited to any particular layout. As imaging progresses, the sample or microarray 12 will be moved in an indexed direction 50 so that each of the grids 48 can be imaged.

An array used in a method described herein can have a plurality of features including, for example, at least about 100, 500, $1 \times 10^3$, $5 \times 10^3$, $1 \times 10^4$, $1 \times 10^5$, $1 \times 10^6$ or more features. In particular embodiments, a bead-based array can be used in which microspheres or beads are arrayed or otherwise spatially distinguished. Exemplary bead-based arrays that can be used in the invention include, without limitation, those in which beads are associated with a solid support such as those described in U.S. Pat. No. 6,355,431 B1; US 2002/0102578; and WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in US 2004/0263923, US 2004/0233485, US 2004/0132205, or US 2004/0125424, each of which is incorporated herein by reference.

Any of a variety of arrays known in the art can be used in the present invention. For example, arrays that are useful in the invention can be non-bead-based. A particularly useful array is an Affymetrix™ GeneChip® array examples of which are described, for example, in U.S. Pat. No. 7,087,732 or U.S. Pat. No. 6,747,143, each of which is incorporated herein by reference. A spotted array can also be used in a method of the invention. An exemplary spotted array is a CodeLink™ Array previously available from Amersham Biosciences. Another array that is useful in the invention is one manufactured using inkjet printing methods such as Sure-Print™ Technology available from Agilent Technologies. Arrays used in various sequencing platforms are also useful such as those used for Solexa sequencing technology as described, for example, in US 2007/0015200; US 2004/0106110; US 20030064398 or US 2003/0022207; those used in 454 sequencing technology such as those described in US 2006/0040297 or U.S. Pat. No. 7,211,390; or those used in Applied Biosystems sequencing methods such as those described in US 2006/0024681 each of which is incorporated herein by reference.

FIG. 4 is an enlarged illustration of one of the grids of the microarray of FIG. 3. As shown in FIG. 4, the grid 48 will be scanned by the imaging system in parallel scan lines 52 that progressively move along the grid. In practice, a point may be scanned over a region of the grid corresponding to each of lines 52. Moreover, in many systems the microarray will be moved slowly, as indicated by arrow 54, while the imaging optic will remain essentially stationary. The parallel lines 52 will then result from the progressive movement of the sample.

In the illustrated embodiment, the grid or region of the microarray has a width 56 which is wider than the length 58 of scan lines of which the imaging system is capable of generating or imaging in each pass. That is, the entire width 56 cannot be scanned or imaged in a single pass. This may be due to the inherent limitation of the line length due to the imaging optics, limitations relating to focusing or movement of components, such as mirrors or other optical components used to generate the scan lines, limitations in digital detectors, and so forth. The area or grid, then, may be scanned in multiple swaths, and values for each of the sites extracted from the image data as mentioned above and as described in greater detail below.

In FIG. 4, for example, the overall width 56 of the grid can be accommodated in two overlapping swaths 60 and 62. The width of each swath, as indicated by reference numeral 64 and 66, respectively, will typically be slightly less than the length 58 of the scan lines. This will permit detection of a feature used to integrate the values derived from the image data, such as by reference to an edge or other feature as described below. It may be noted that a common area or overlap 68 exists that is imaged in both swaths. The present technique allows for identification of sites within this overlap area and the use of one of the values only to avoid redundancy, or the use of a combination of the values once these have been properly indexed.

Figure 5:
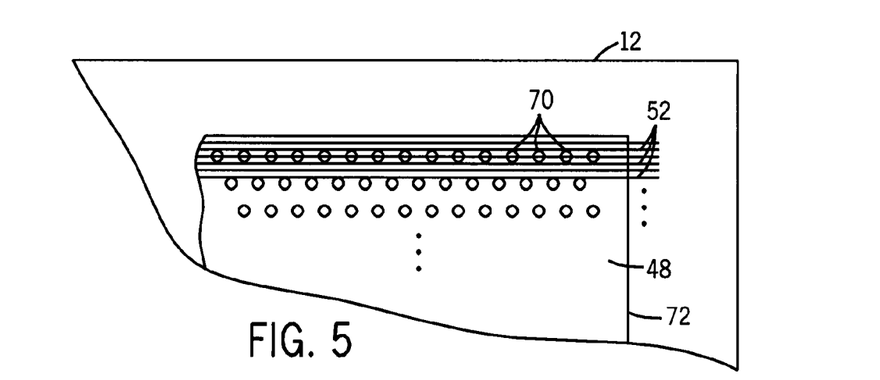
FIG. 5 is a further enlarge view of a portion of the microarray of FIGS. 3 and 4 illustrating individual sites on the microarray.

FIG. 5 illustrates in somewhat greater detail scan lines 52 over a plurality of sites 70 in the grid 48 illustrated in FIG. 4. As noted above, the sites may be laid out in any suitable grid pattern, or even randomly. In the illustrated embodiment, for example, the sites are laid out in a generally hexagonal pattern, although rectangular patterns, and other patterns may be employed. The location of each site will typically be known with reference to one or more fiducial features, such as an edge 72 of the grid or portion of the microarray. In the case of random site locations, these may be located and mapped by an initial imaging sequence designed to detect the location of all sites of interest.

Figure 6:
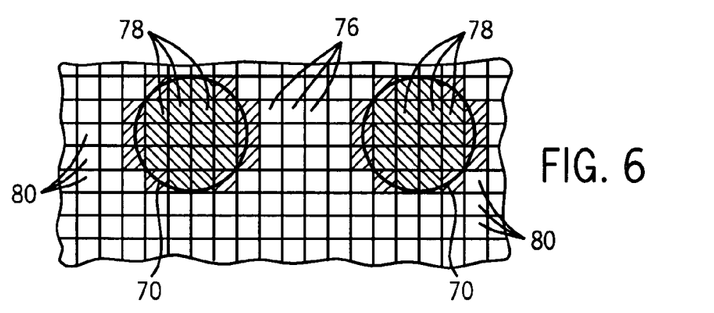
FIG. 6 is a detailed view of a pixilated image of sites on a microarray of the type illustrated in FIG. 5.

FIG. 6 represents a portion of an exemplary image of the type that will be generated based upon image data collected by progressive scanning of the region of interest in the microarray. The actual image 74 is composed of a large number of pixels 76 each of which corresponds to a digital value from the imaging system. The pixel data, which represents the image, will encode values corresponding to bright pixels 78 and darker pixels 80. In practice, various grey levels or even color encoding can be employed such that the individual sites 70 can be identified by detecting contrast between the pixels as indicated by their individual digital values.

Figure 7:
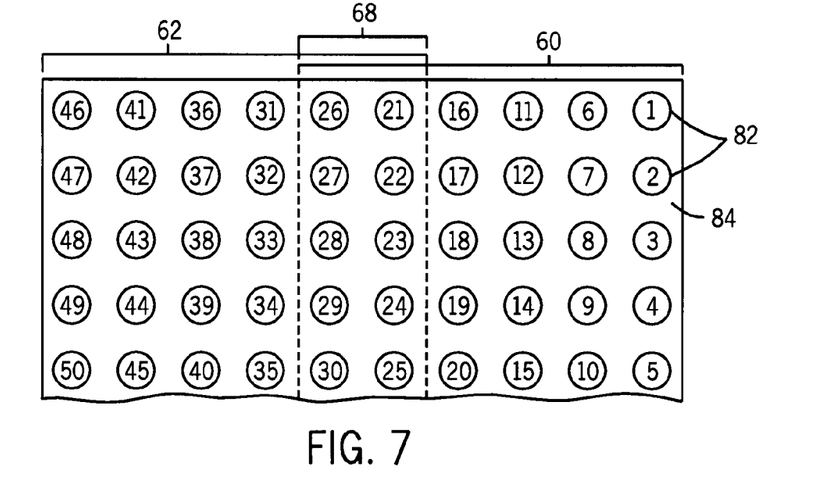
FIG. 7 is a diagrammatical representation of an exemplary index map for a microarray of the type illustrated in FIG. 5.

FIG. 7 is an exemplary representation of a simplified mapping of sites in a microarray of the type discussed above. A map of sites can be created using methods known in the art. For example, the identity of the probes at particular features of a random array can be determined by a decoding process such as those described in Gunderson et al., *Genome Res.* 14:870-877 (2004); US 2003/0157504 or U.S. Pat. No. 7,033,754, each of which is incorporated herein by reference. Whether probe identity is determined by decoding or by ordered placement, a map of sites can be created by reference to an aligned grid or to other fiducial marks as described, for example, in US 2002/0150909; Galinsky, *Bioinformatics,* 19: 1824-1831 (2003); Galinsky, *Bioinformatics,* 19: 1832-1836, (2003) or U.S. Pat. No. 6,090,955, each of which is incorporated herein by reference.

As illustrated in FIG. 7, each site location is generally known and is assigned an index designation 82, such as a series integer progressing over the entire grid area or microarray area. The collection of locations and index designations may be compiled into an index map 84 which may be viewed in an operator interface, and more particularly, is used to assign values to individual locations on the microarray.

As discussed above, based upon the digital values of the cluster of pixels corresponding to each site, as represented generally in FIG. 6, a value for the individual site may be assigned. This value may correspond, for example, to the nucleotide most prevalent at the individual site as indicated by the wavelength or intensity or other characteristic of the cluster of pixels. As mentioned above, and as discussed in greater detail below, a value will be assigned to each site corresponding to a particular characteristic. In a typical application for DNA imaging, four such values may be employed, although more or fewer values may be used in any particular application. These values, then, are associated with the index locations, as shown in the simplified example of FIG. 7, and the corresponding sets of values and indices are stored in memory for stitching as described below. It should be noted that, as illustrated in FIG. 7, where multiple swaths are imaged, some of the indexed locations will be part of both the first swath and the second swath.

Figure 8:
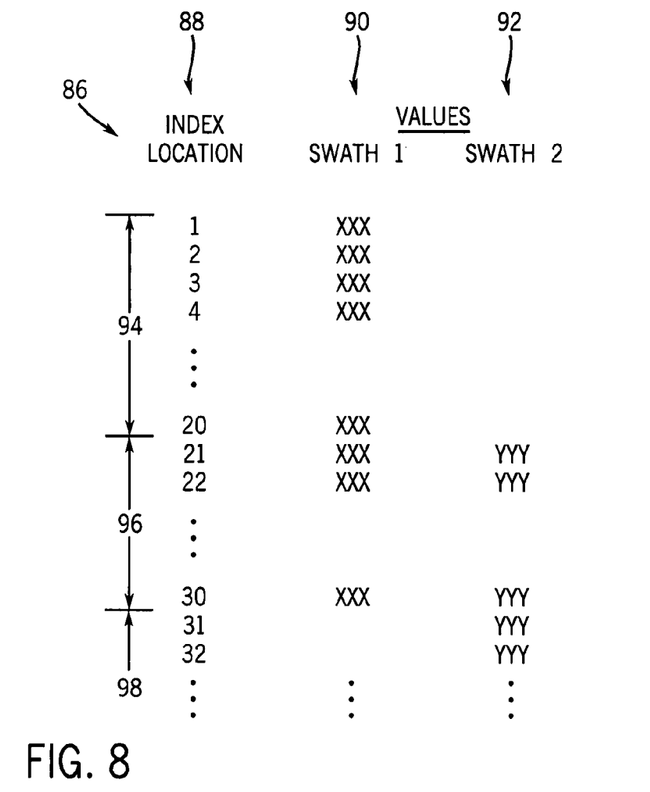
FIG. 8 is an illustration of exemplary tabulated data for multiple swaths, illustrating and exemplary manner in which the data may be integrated in accordance with the present technique.

FIG. 8 illustrates an exemplary tabulated presentation of index designations from FIG. 7 associated with values of sites for each indexed location. That is, as shown in FIG. 8, tabulated data 86 represents indexed locations as indicated by column 88, with associated values for each site as indicated by columns 90 and 92. The index locations will correspond to individual site designations as illustrated in FIG. 7, and the individual swaths, labeled 60 and 62 in FIG. 7, along with the overlapping region labeled 68, will generally appear in the tabulated data of FIG. 8 as lengths or series 94, 98 and 96, respectively of indexed values. That is, considering FIGS. 7 and 8 together, all indexed locations will have a corresponding value assigned to them, even if the site is dark. In that event, the value assigned may be zero. The indexed locations of swath 60 will correspond to the portion of the tabulated data indicated by reference numeral 94, extending from site 1 to site 20, as well as the data for sites 21-30 in this example. Sites 21-30 also form part of swath 62, along with further sites 31-50. The individual values assigned to each site location are indicated by a XXX for the first swath and YYY for the second swath (although these values will typically differ for different nucleotides). The simplified example of FIG. 8 indicates simply that a value is assigned for each of the indexed sites.

Evaluation of the data will easily reveal the overlapping region 68 illustrated in FIG. 7, corresponding to the series 96 of FIG. 8 because values will be assigned to each indexed site in both swaths.

It should be noted that tabulating the data as illustrated in FIG. 8 may be done in such a way as to present the data to a human operator, store the tabulated data, or even display the tabulated data graphically. However, in some implementations it is contemplated that the tabulated information will not actually be displayed for the user, but the data integration will simply be automated, and resulting values for each indexed location will be stored. It should also be noted that in the embodiment just described, sites in the first and second swaths are indexed by reference to the edge, left and right of the grid region imaged. That is, in the first swath, the rightmost sites are known to correspond to the first column of the map, whereas the left-most sites in the second swath are known to correspond to the left column of the map. Other fiducial features may also be relied upon for indexing the site values. These may include, as described below, notches, grids, regions of particular optical properties (reflective, designated colors, and so forth), locations of known control substances (e.g., nucleotides or oligonucleotides) and so forth.

In a presently contemplated embodiment, the data stitching calls for storing only one of the values in the overlapping region. Thus, in the foregoing example, region 68 shown in FIG. 7 is comprised of number of sites that include values for both the first swath and the second swath as indicated by reference numeral 96 in FIG. 8. In this presently contemplated embodiment, the first values imaged are retained due to the potential for bleaching that can result from subsequent scanning (i.e., in the second swath). However, other techniques may be employed including storing of the second assigned value, storing of both assigned values, or blending of the two values in an average or other function.

Figure 9:
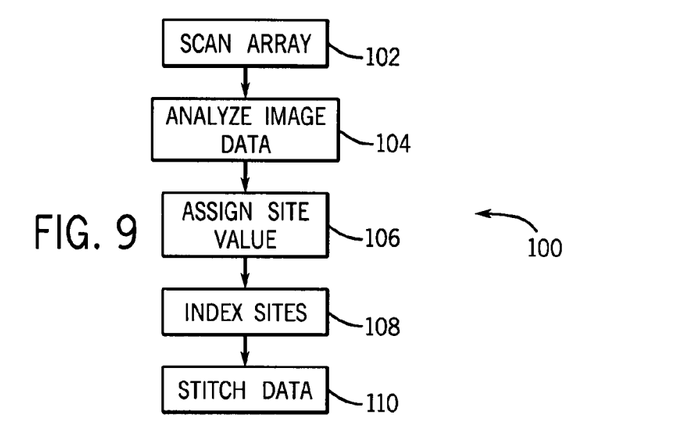
FIG. 9 is a flow chart of exemplary logic for carrying out the present technique.

FIG. 9 represents exemplary steps in the foregoing technique. The logic of the technique designated generally by reference numeral 100, begins with scanning the microarrays as indicated at step 102 to produce image data which is pixilated in the manner that allows for identification of individual sites and assignment of values to these sites. At step 104, then, the digitized image data is analyzed to identify the location of the imaged sites and groupings of pixels that comprise each site. At step 106 a value is assigned to each site which, again, may be based upon intensity of the grouping of pixels, color, or any other desired characteristic. Based upon the location of each of these sites, then, the sites are indexed as indicated at step 108, and each value for each site is associated with an index value. Finally, at step 110, the data is stitched by comparing values for each of the indexed sites in the individual swaths to determine which sites were imaged more than once, and the resulting stitched data may be stored.

Figure 10:
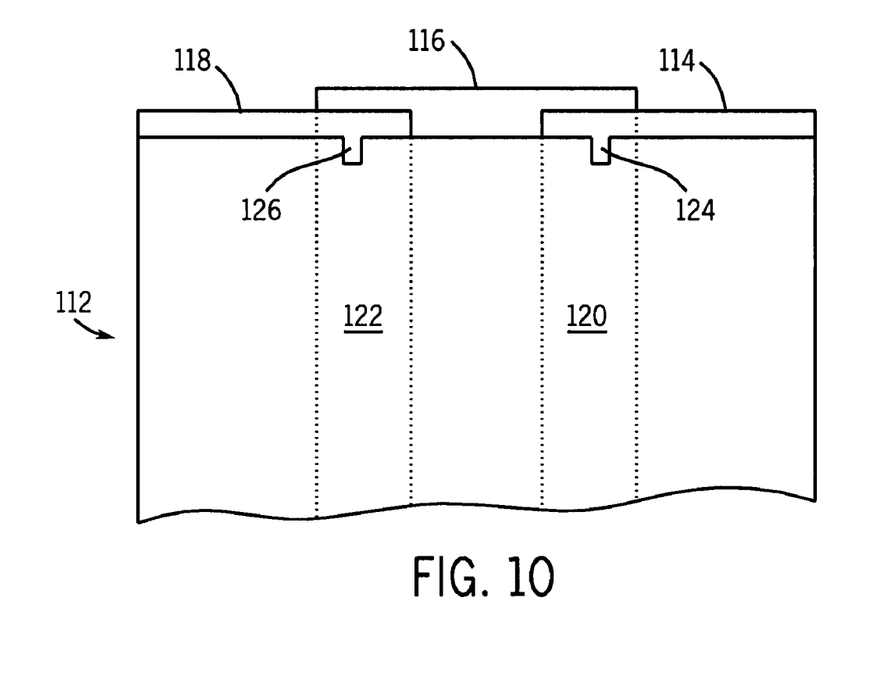
FIG. 10 is a diagrammatical view of a portion of a biological microarray in which more than two swaths are imaged and the present technique is used for integrating the data derived from the image data.
Figure 11:
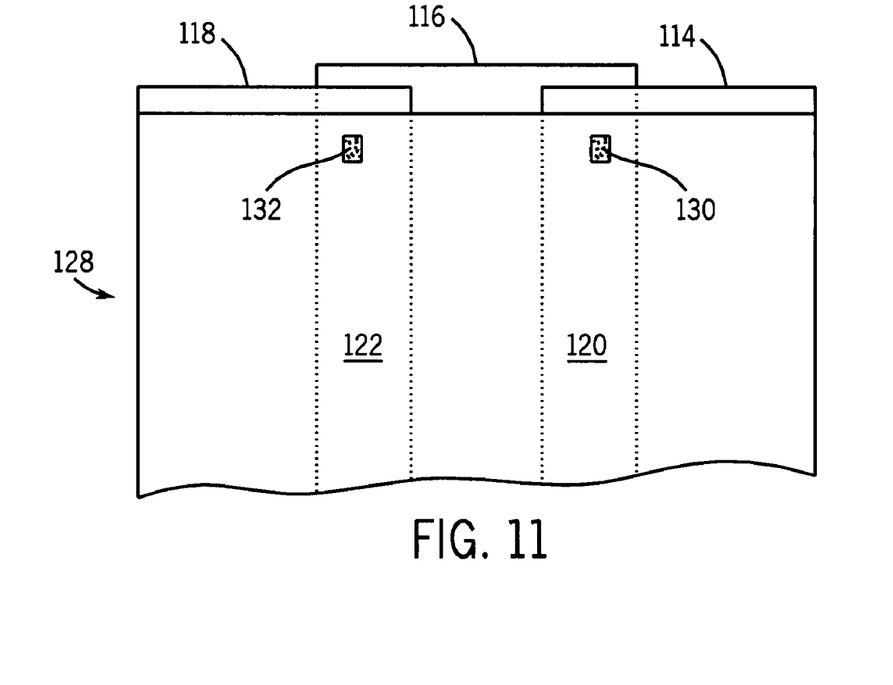
FIG. 11 is a similar view of an alternative configuration for a multiple swath imaging approach utilizing the present invention.

While in the foregoing description reference was made to imaging with two swaths, the present technique allows for imaging with any number of overlapping swaths. FIGS. 10 and 11 illustrate such embodiments. In the illustration of FIG. 10, for example, a multi-swath region 112 includes overlapping swaths 114, 116 and 118. Because the entire region is too wide to be imaged in one pass, or even two passes, the multiple swaths may be imaged independently with overlapping regions 120 and 122 included to ensure that all sites are imaged and analyzed. Because the middle swath 116 will not be adjacent to a side edge, and therefore, cannot use a side edge as a fiducial feature, notches 124 and 126 may be provided which can be easily located in both of the overlapping regions 120 and 122 to facilitate identification of which sites are located in which locations in the index mapping. In some applications, it may be possible to use the upper edge of the region rather than such notches.

In the manner illustrated in FIG. 11, similar data stitching is performed with fiducial markers 130 and 132 used for location purposes. That is, regions having specific optical properties, or more generally properties that permit clearly identifying their locations in the resulting image data, are used to identify locations of individual sites in the image data within the overlapping regions 120 and 122. This permits the individual sites to be appropriately located for each of the swaths, and the subsequent mapping of site values to the indexed locations. Similar techniques may be used for imaging any number of swaths with overlapping regions.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for analyzing a biological microarray comprising:
   accessing image data for a plurality of imaged swaths of the microarray;
   assigning a value to each of a plurality of sites in each swath based upon the image data;
   associating each site value with a corresponding location index; and
   combining the site values for the swaths based upon the location indices wherein the steps of the method are performed on a processor.

2. The method of claim 1, wherein the swaths overlap, and each of a plurality of sites of a first swath in an overlapping region are assigned the same location index as a respective site of the second swath in the overlapping region.

3. The method of claim 2, wherein the site values are combined by retaining only one of the values for the sites of the overlapping region.

4. The method of claim 3, wherein the site values are combined by retaining only values of sites in the swath that was first imaged.

5. The method of claim 1, wherein the site values are representative of a nucleic acid present at each site as indicated by the image data.

6. The method of claim 1, wherein the site values are assigned by analysis of image data for a plurality of pixels at each site.

7. The method of claim 1, wherein the site values are associated with the location indices by reference to a known feature of the microarray.

8. The method of claim 7, wherein the known feature is an edge of an area of the microarray in which the sites are located.

9. The method of claim 7, wherein the known feature is a fiducial mark or feature located in a region where the swaths overlap.

10. The method of claim 7, wherein the known feature is a unique pattern of sites in said microarray.

11. A method for analyzing a biological microarray comprising:
accessing image data for a plurality of imaged overlapping first and second swaths of the microarray;
assigning a value to each of a plurality of sites in each swath based upon the image data;
associating each site value with a corresponding location index by reference to a known feature of the microarray, each of a plurality of sites of the first swath in an overlapping region being assigned the same location index as a respective site of the second swath in a region where the swaths overlap; and
combining the site values for the swaths based upon the location indices wherein the steps of the method are performed on a processor.

12. The method of claim 11, wherein the site values are combined by retaining only one of the values for the sites of the overlapping region.

13. The method of claim 12, wherein the site values are combined by retaining only values of sites in the swath that was first imaged.

14. The method of claim 11, wherein the site values are representative of a nucleic acid present at each site as indicated by the image data.

15. The method of claim 11, wherein the site values are assigned by analysis of image data for a plurality of pixels at each site.

16. The method of claim 11, wherein the site values are associated with the location indices by reference to a known feature of the microarray.

17. The method of claim 16, wherein the known feature is an edge of an area of the microarray in which the sites are located.

18. The method of claim 16, wherein the known feature is a fiducial mark or feature located in a region where the swaths overlap.

19. A system for analyzing a biological microarray comprising:
image data for a plurality of imaged swaths of the microarray; and
a processor configured to assign a value to each of a plurality of sites in each swath based upon the image data, to associate each site value with a corresponding location index, and to combine the site values for the swaths based upon the location indices.

20. The system of claim 19, comprising an imaging system configured to generate the imaging data for the swaths of the microarray.

21. The system of claim 20, wherein the imaging system scans each swath with a line of radiation that is longer than a width of the swaths, but shorter than a combined width of the swaths.

22. A system for analyzing a biological microarray comprising:
an imaging system configured to generate the imaging data for a plurality of swaths of the microarray;
a memory circuit configured to store image data for a plurality of imaged swaths generated by the imaging system; and
a processor configured to assign a value to each of a plurality of sites in each swath based upon the image data, to associate each site value with a corresponding location index by reference to a known feature of the microarray, each of a plurality of sites of the first swath in an overlapping region being assigned the same location index as a respective site of the second swath in a region where the swaths overlap, and to combine the site values for the swaths based upon the location indices.

23. A non-transitory machine readable medium storing code executable by a computer for performing the method recited in claim 1.

24. A non-transitory machine readable medium storing code executable by a computer for performing the method recited in claim 10.

* * * * *